United States Patent [19]
Fujita et al.

[11] Patent Number: 5,693,832
[45] Date of Patent: Dec. 2, 1997

[54] HYDROFORMYLATION OF ALLYL ALCOHOL

[75] Inventors: Tetsuro Fujita; Kenichiro Maki; Kuniomi Marumo, all of Oita, Japan

[73] Assignee: Showa Denko K.K., Tokyo, Japan

[21] Appl. No.: 266,268

[22] Filed: Jun. 27, 1994

[51] Int. Cl.$^6$ .................................. C07D 307/20
[52] U.S. Cl. ........................... 549/475; 549/479
[58] Field of Search ........................ 549/475, 479; 568/451, 454

[56] References Cited

PUBLICATIONS

Chemical Abstract, 113 : 96687e, 1990.
Chemical Abstract, 117 : 90724a, 1992.

*Primary Examiner*—Ba K. Trinh
*Attorney, Agent, or Firm*—Sughrue, Mion, Zinn, Macpeak & Seas, PLLC

[57] ABSTRACT

A process for the hydroformylation of allyl alcohol is disclosed, which comprises reacting allyl alcohol with carbon monoxide and hydrogen in the presence of a rhodium compound and a diphosphine compound represented by formula (I) or (II)

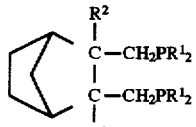

(I)

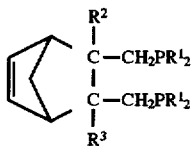

(II)

wherein $R^1$ represents an alkyl group or a substituted or unsubstituted aryl group; and $R^2$ and $R^3$ each represents an alkyl group or a hydrogen atom.

8 Claims, No Drawings

HYDROFORMYLATION OF ALLYL ALCOHOL

FIELD OF THE INVENTION

This invention relates to a process for the hydroformylation of allyl alcohol. 2-Hydroxytetrahydrofuran obtained by the process of the present invention can be easily converted into 1,4-butanediol by reducing it in the presence of hydrogen. The resulting 1,4-butanediol is very useful as a starting material for the preparation of polybutylene terephthalate and urethane resins and as a starting material for the preparation of tetrahydrofuran which is an excellent solvent.

BACKGROUND OF THE INVENTION

It is well known that when olefinic compounds are reacted with carbon monoxide and hydrogen in the presence of a Group IX metal complex compound such as a rhodium complex compound or a complex using triphenylphosphine as a ligand (unidenrate ligand) to carry out hydroformylation, the reaction rate, the conversion rate of the olefins, the types and amounts of by-products formed, and the selectivity and yields of the desired straight-chain or branched oxo compounds are greatly affected by the types and amounts of the olefinic compounds and ligands.

A similar phenomenon to that described above occurs in the hydroformylation of allyl alcohol. Many attempts have been made to obtain 2-hydroxytetrahydrofuran with high selectivity which is the precursor of 1,4-butanediol while the formation of main by-products, 2-methyl-3-hydroxypropanal, propionaldehyde and n-propanol, is suppressed. It was found that the selectivity of the desired product is greatly varied by the types of the ligands to be added to the reaction system.

For example, JP-A-51-29412 (the term "JP-A" as used herein means an "unexamined published Japanese patent application") discloses that a catalyst comprising a combination of hydridocarbonyltris(triphenylphosphine)rhodium (I) industrially used in the hydroformylation of propylene with triphenylphosphine (unidentate ligand) is applied to allyl alcohol, thereby obtaining 2-hydroxytetrahydrofuran with selectivity of 75 to 79%. The straight-chain aldehyde formed by the hydroformylation of allyl alcohol is 4-hydroxybutyl aldehyde. It is reported that the aldehyde is isomerized and is present as more stable 2-hydroxytetrahydrofuran (see, C. U. Pittman, Jr., *Journal of Organic Chemistry*, Vol. 45, page 2132 (1980)).

Further, C. U. Pittman, Jr. (*Journal of Organic Chemistry*, Vol. 45, page 2132 (1980)) reports that when triphenylphosphine (unidentate ligand) is used as the ligand, the selectivity of 2-hydroxytetrahydrofuran is 67% (normal/iso ratio being 2.0). When tributylphosphine (unidentate ligand) is used, the selectivity is 40% (a large amount of a high-boiling product being formed). When 1,1'-bis(diphenylphosphino)ferrocene (bidentate ligand) is used, the selectivity is 75% (normal/iso ratio being 3.3). The literature teaches that it is necessary that a ligand which is most suitable for allyl alcohol is chosen to obtain the straight-chain product with high selectivity since there are great changes in the reaction results depending on the types of the ligands.

JP-A-54-106407 discloses that it is found that the life of the catalyst is improved when there is used a three-component catalyst obtained by adding a diphosphinoalkane (bidentate ligand) such as typically 1,4-bis (diphenylphosphino)butane to the above catalyst comprising the rhodium complex compound and triphenylphosphine (unidentate ligand). However, the selectivity of 2-hydroxytetrahydrofuran is 75 to 79%. Namely, the selectivity is not improved by adding the diphosphinoalkane. Further, about 10% (in terms of selectivity) of undesired by-products, propionaldehyde and n-propanol, in addition to the isomer, 2-methyl-3-hydroxypropanal, are formed.

JP-A-53-121711 discloses that the selectivity of the straight-chain product can be improved when hydroformylation is carried out by using a diphosphine cyclic compound as a ligand which has such a structure that two carbon atoms adjacent to each other in the ring are substituted by two phosphinomethyl groups which are located at the transpositions from each other. This patent specification shows an embodiment wherein trans-1,2-bis (diphenylphosphinomethyl)cyclobutane is used. However, there is found no concrete example wherein allyl alcohol is used as a substrate in the specification.

JP-A-56-26830 discloses that the life of the catalyst can be improved when the hydroformylation reaction is carried out by using a ternary catalyst comprising a rhodium compound, a diphosphine compound (bidentate ligand) and a tri-substituted phosphine (unidentate ligand), said diphosphine compound having such a structure that two carbon atoms adjacent to each other on an alicyclic hydrocarbon ring having 3 to 6 carbon atoms are substituted by two phosphinomethyl groups which are located at the transpositions from each other. There are described examples wherein trans-1,2-bis(diphenylphosphinomethyl) cyclobutane and trans-1,2-bis-(diphenylphosphinomethyl) cyclopentane are used. However, there is found no example wherein allyl alcohol is used in the specification. Further, there is no explicit description with regard to an effect on the selectivity of the straight-chain product.

As described above, attempts have been made to obtain 2-hydroxytetrahydrofuran with good selectivity which is useful as a precursor of 1,4-butanediol, by making extensive studies on various catalyst ligands in the hydroformylation reaction system wherein allyl alcohol is reacted with carbon monoxide and hydrogen in the presence of a rhodium complex compound. However, since the effect of the catalyst ligands greatly varies depending on the types of the reaction substrates, a sufficient effect cannot be obtained unless the ligand used in the catalyst for the hydroformylation reaction of allyl alcohol is suitable for allyl alcohol in particular. The reaction system using allyl alcohol as the substrate has a problem in that the selectivity of industrially desirable straight-chain product is low, and propionaldehyde (which is an isomerized product of allyl alcohol) and n-propanol (which is a hydrogenated product of allyl alcohol) are by-produced, in contrast to the hydroformylation of simple olefins. A process for producing 2-hydroxytetrahydrofuran with high selectivity without forming these by-products has not been proposed.

SUMMARY OF THE INVENTION

Accordingly, an object of the present invention is to provide a process for the hydroformylation of allyl alcohol which enables the selectivity of the by-products to be greatly reduced and allows 2-hydroxytetrahydrofuran with high selectivity to be obtained in the hydroformylation process which comprises reacting allyl alcohol with carbon monoxide and hydrogen in the presence of a rhodium complex compound.

The present inventors have made studies on the effect on the addition of many organophosphorus ligands to solve the above-described problems. As a result, we have found that when diphosphine compounds (bidentate ligand) having a specific structure are used, the selectivity of propionaldehyde and n-propanol by-produced can be remarkably reduced, and the selectivity of the straight-chain product can be greatly improved. The present invention has been achieved on the basis of the above finding.

The above-described object of the present invention has been achieved by a process for the hydroformylation of allyl alcohol which comprises reacting allyl alcohol with carbon monoxide and hydrogen in the presence of a rhodium compound and a diphosphine compound represented by formula (I) or (II)

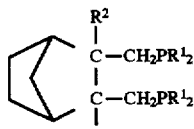     (I)

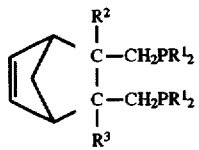     (II)

wherein $R^1$ represents an alkyl group or a substituted or unsubstituted aryl group; and $R^2$ and $R^3$ each represents an alkyl group or a hydrogen atom.

DETAILED DESCRIPTION OF THE INVENTION

In conventional formylation reaction of allyl alcohol, there is a problem that the selectivity of the industrially desirable straight-chain product is low as described above. The process of the present invention is freed from the problem associated with prior art. According to the hydroformylation reaction of the present invention, there can be obtained 2-hydroxytetrahydrofuran with very high selectivity which is a precursor of 1,4-butanediol.

In formulae (I) and (II), $R^1$ is preferably an unsubstituted aryl group, and $R^2$ and $R^3$ each preferably represents a hydrogen atom or a methyl group. The norbornane ring and the norbornene ring in formulae (I) and (II), respectively, may have an alkyl group as a substitutent on the ring-forming carbon atom(s) other than the carbon atoms substituted with the groups —$CH_2PR^1{}_2$, $R^2$ and $R^3$.

Examples of the diphosphine compound (bidentate ligand) of formula (I) or (II) include trans-2,3-bis(diphenylphosphinomethyl)bicyclo-[2,2,1]-heptane (hereinafter referred to as "reDPMNr"), trans-2,3-bis(diphenylphosphinomethyl)-bicyclo-[2,2,1]-hept-5-ene (hereinafter referred to as "DPMNr"), trans-2,3-bis-(diphenylphosphinomethyl)-2-methyl-bicyclo-[2,2,1]-heptane, trans-2,3-bis(diphenylphosphinomethyl)-2-methyl-bicyclo-[2,2,1]-hept-5-ene, trans-2,3-bis (diphenylphosphinomethyl)-1,4,5,6,7-pentamethyl-bicyclo-[2,2,1]-heptane, trans-2,3-bis-(diphenylphosphinomethyl)-1,4,5,6,7-pentamethyl-bicyclo-[2,2,1]-hept-5-ene, trans-2,3-bis(diphenylphosphinomethyl)-1,2,4,5,6,7-hexamethyl-bicyclo-[2,2,1]-heptane and trans-2,3-bis (diphenylphosphinomethyl)-1,2,4,5,6,7-hexamethyl-bicyclo-[2,2,1]-hept-5-ene. Of these compounds, reDPMNr and DPMNr are particularly preferred from the standpoint of the effect of the present invention.

It is desirable from the standpoint of enhancing the selectivity of 2-hydroxytetrahydrofuran that the diphosphine compound is used in an amount of 0.5 to 50 mol, preferably 1.5 to 10 mol, per 1 gram-atom of rhodium. When the amount of the diphosphine compound used is less than 0.5 mol, the selectivity of the straight-chain product is lowered, while when the amount is more than 50 mol, the reaction rate is lowered, and hence such an amount is economically disadvantageous.

In addition to the above-described phosphine compounds (bidentate ligand), tri-substituted phosphines (unidentate ligand) may preferably be added in the hydroformylation reaction system of the present invention. The tri-substituted phosphine which can be added is represented by formula (III)

$PR^4R^5R^6$     (III)

wherein $R^4$, $R^5$ and $R^6$ each represents an alkyl group, preferably having 2 to 7 carbon atoms, or a substituted or unsubstituted aryl group.

Examples of the tri-substituted phosphines of formula (III) include triphenylphosphine, tri-p-tolylphosphine, tri-m-tolylphosphine, tris(p-methoxyphenyl)phosphine, tris(m-methoxyphenyl)phosphine, tris(p-chlorophenyl)phosphine, tris-(m-chlorophenyl)phosphine, tris(p-fluorophenyl) phosphine, tris(m-fluorophenyl)phosphine, tris(p-trifluoromethylphenyl)-phosphine, triethylphosphine, triisopropylphosphine, tributylphosphine, tricyclohexylphosphine, ethyldiphenylphosphine and diethylphenylphosphine. Of these, triphenylphosphine and tris(p-fluorophenyl)phosphine are preferred. The tri-substituted phosphines are preferably used in an amount of 2 to 500 mol, more preferably 50 to 350 mol, per 1 gram-atom of rhodium.

Any of rhodium compounds conventionally used for catalysts for the hydroformylation of olefins can be used in the present invention. Specific examples of the rhodium compounds include rhodium oxides such as RhO, $Rh_2O_3$ and $RhO_2$; rhodium salts such as rhodium nitrate, rhodium sulfate, rhodium chloride, rhodium bromide, rhodium iodide and rhodium acetate; rhodium complex compounds such as acetylacetonatodicarbonylrhodium (hereafter referred to as "$Rh(acac)(CO)_2$"), acetylacetonatocarbonyl (triphenylphosphine)rhodium and hydridocarbonyltris (triphenylphosphine)rhodium; and rhodium carbonyl clusters such as $Rh_4(CO)_{12}$ and $Rh_6(CO)_{16}$.

The catalyst is used in such an amount that the amount of rhodium in the catalyst is in the range of preferably $1\times10^{-2}$ to $1\times10^{-4}$ gram-atom per mol of allyl alcohol, though there is no particular limitation with regard to the amount of the catalyst.

It is preferred that solvents used in the present invention are inert to allyl alcohol and the product. Specific examples of the solvents include aromatic hydrocarbons such as benzene, toluene, xylene, ethylbenzene and dodecylbenzene; saturated hydrocarbons such as n-hexane, heptane, cyclohexane and methylcyclohexane; ethers such as diethyl ether and diphenyl ether; and esters of carboxylic acids such as methyl acetate, ethyl acetate, diethyl phthalate, dibutyl phthalate and dioctyl phthalate. Of these compounds, aromatic compounds such as benzene, toluene, xylene, ethylbenzene, dodecylbenzene, diethyl phthalate, dibutyl phthalate and dioctyl phthalate are particularly preferred. Usually, the solvents are used in an amount of 2 to 50 times by volume the amount of allyl alcohol, though there is no particular limitation with regard to the amount of the solvents to be used.

The reaction temperature in the hydroformylation of the present invention is preferably 40° to 100° C., particularly preferably 50° to 80° C. When the reaction temperature is lower than 40° C., the reaction rate is extremely low, while when the reaction temperature is higher than 100° C., the selectivity of 2-hydroxytetrahydrofuran is lowered, and at the same time, the stability of the catalyst is deteriorated.

Carbon monoxide and hydrogen are introduced in the reaction system as a mixed gas, and the carbon monoxide/hydrogen ratio (by mol) is preferably from 1/10 to 10/1. There is no particular limitation with regard to the reaction pressure. However, it is practically preferred that the reaction is carried out under a pressure of 1 to 20 atm.

The present invention is now illustrated in greater detail with reference to the following examples which, however, are not to be construed as limiting the invention.

EXAMPLE 1

Into a 50 ml autoclave equipped with a thermometer and a stirrer were charged 2.0 g (34.4 mmol) of allyl alcohol, 5.16 mg (20 µmol) of $Rh(acac)(CO)_2$, 19.7 mg (40 µmol) of reDPMNr and 16 ml of toluene. While the mixture was stirred, the autoclave was thoroughly purged with nitrogen gas and then with a $CO/H_2$ mixed gas. The mixture was heated until the temperature of the mixed solution reached a constant temperature of 65° C. Subsequently, a $CO/H_2$ (1/1 by mol) mixed gas was introduced into the autoclave until pressure in the autoclave reached 6.0 atm, and the reaction was commenced. Further, a $CO/H_2$ (1/1 by mol) mixed gas was introduced thereinto so as to keep pressure in the reaction system at 6.0 atm during the course of the reaction. In this manner, the hydroformylation reaction of allyl alcohol was carried out under constant temperature and pressure conditions. The quantitative analysis of the reaction products was made by gas chromatography. All of the products were isolated and identified by $^1H$ and $^{13}C$-NMR analysis.

Three hours after the reaction was commenced, the conversion rate of allyl alcohol was 97.9%. It was found that 2.59 g (29.4 mmol) of 2-hydroxytetrahydrofuran and 0.362 g (4.11 mmol) of 2-methyl-3-hydroxypropanal were produced. The selectivity of 2-hydroxytetrahydrofuran was 87.2 mol % (hereinafter simply referred to as %). The selectivity of 2-methyl-3-hydroxypropanal, that of propionaldehyde and that of n-propanol were 12.2%, 0.14% and 0.13%, respectively.

EXAMPLE 2

The hydroformylation reaction of allyl alcohol was carried out in the same manner as in Example 1 except that 39.4 mg (80 µmol) of reDPMNr was added, the pressure was 9.0 atm, and the reaction temperature was 55° C. Six hours after the reaction was commenced, the conversion rate of allyl alcohol was 94.3%. It was found that 2.54 g (28.8 mmol) of 2-hydroxytetrahydrofuran and 0.303 g (3.44 mmol) of 2-methyl-3-hydroxypropanal were produced. The selectivity of 2-hydroxytetrahydrofuran was 88.8%. The selectivity of 2-methyl-3-hydroxypropanal, that of propionaldehyde and that of n-propanol were 10.6%, 0.17% and 0.15%, respectively.

EXAMPLE 3

The hydroformylation reaction of allyl alcohol was carried out in the same manner as in Example 1 except that 19.7 mg (40 µmol) of DPMNr was added in place of reDPMNr. After 3 hours, the conversion rate of allyl alcohol was 99.9%. It was found that 2.58 g (29.3 mmol) of 2-hydroxytetrahydrofuran and 0.423 g (4.82 mmol) of 2-methyl-3-hydroxypropanal were produced. The selectivity of 2-hydroxytetrahydrofuran was 85.1%. The selectivity of 2-methyl-3-hydroxypropanal, that of propionaldehyde and that of n-propanol were 14.0%, 0.15% and 0.13%, respectively.

EXAMPLE 4

The hydroformylation reaction of allyl alcohol was carried out in the same manner as in Example 1 except that 262 mg (1.0 mmol) of triphenylphosphine in addition to reDPMNr was added. Three hours after the reaction was commenced, the conversion rate of allyl alcohol was 90.5%. It was found that 2.40 g (27.3 mmol) of 2-hydroxytetrahydrofuran and 0.330 g (3.75 mmol) of 2-methyl-3-hydroxypropanal were produced. The selectivity of 2-hydroxytetrahydrofuran was 87.6%. The selectivity of 2-methyl-3-hydroxypropanal, that of propionaldehyde and that of n-propanol were 12.0%, 0.16% and 0.13%, respectively.

EXAMPLE 5

The hydroformylation reaction of allyl alcohol was carried out in the same manner as in Example 1 except that 316 mg (1.0 mmol) of tris(p-fluorophenyl)phosphine in addition to reDPMNr was added. After 4.5 hours from the commencement of the reaction, the conversion rate of allyl alcohol was 94.1%. It was found that 2.53 g (28.7 mmol) of 2-hydroxytetrahydrofuran and 0.313 g (3.56 mmol) of 2-methyl-3-hydroxypropanal were produced. The selectivity of 2-hydroxytetrahydrofuran was 88.8%. The selectivity of 2-methyl-3-hydroxypropanal was 11.0%, and propionaldehyde and n-propanol were not detected.

EXAMPLE 6

The hydroformylation reaction of allyl alcohol was carried out in the same manner as in Example 1 except that 3.53 mg (3.33 µmol) of $Rh_6(CO)_{16}$ was used as the Rh compound in place of $Rh(acac)(CO)_2$. Three hours after the reaction was commenced, the conversion rate of allyl alcohol was 91.5%. It was found that 2.41 g (27.4 mmol) of 2-hydroxytetrahydrofuran and 0.310 g (3.52 mmol) of 2-methyl-3-hydroxypropanal were produced. The selectivity of 2-hydroxytetrahydrofuran was 86.9%. The selectivity of 2-methyl-3-hydroxypropanal, that of propionaldehyde and that of n-propanol were 11.2%, 1.08% and 0.29%, respectively.

COMPARATIVE EXAMPLE 1

The hydroformylation reaction of allyl alcohol was carried out in the same manner as in Example 1 except that 21.0 mg (80 µmol) of triphenylphosphine was added in place of reDPMNr. Three hours after the reaction was commenced, the conversion rate of allyl alcohol was 100%. It was found that 1.87 g (21.2 mmol) of 2-hydroxytetrahydrofuran and 1.14 g (12.9 mmol) of 2-methyl-3-hydroxypropanal were produced. The selectivity of 2-hydroxytetrahydrofuran was 61.6%. The selectivity of 2-methyl-3-hydroxypropanal and that of propionaldehyde were 37.5% and 0.85%, respectively. n-Propanol was not detected.

COMPARATIVE EXAMPLE 2

The hydroformylation reaction of allyl alcohol was carried out in the same manner as in Example 1 except that 17.1 mg (40 µmol) of 1,4-bis(diphenylphosphino)butane was added in place of reDPMNr. Three hours after the reaction was commenced, the conversion rate of allyl alcohol was 97.9%. It was found that 1.91 g (21.7 mmol) of 2-hydroxytetrahydrofuran and 0.866 g (9.83 mmol) of 2-methyl-3-hydroxypropanal were produced. The selectivity of 2-hydroxytetrahydrofuran was 65.7%. The selectivity of 2-methyl-3-hydroxypropanal, that of propionaldehyde and that of n-propanol were 29.8%, 1.75% and 0.65%, respectively.

COMPARATIVE EXAMPLE 3

The hydroformylation reaction of allyl alcohol was carried out in the same manner as in Example 1 except that 18.1 mg (40 µmol) of trans-1,2-bis(diphenylphosphinomethyl)-cyclobutane was added in place of reDPMNr. Six hours after the reaction was commenced, the conversion rate of allyl alcohol was 90.2%. It was found that 2.79 g (24.5 mmol) of 2-hydroxytetrahydrofuran and 0.610 g (5.37 mmol) of 2-methyl-3-hydroxypropanal were produced. The selectivity of 2-hydroxytetrahydrofuran was 79.0%. The selectivity of 2-methyl-3-hydroxypropanal, that of propionaldehyde and that of n-propanol were 17.3%, 2.10% and 0.09%, respectively.

COMPARATIVE EXAMPLE 4

The hydroformylation reaction of allyl alcohol was carried out in the same manner as in Example 1 except that 18.7 mg (40 µmol) of trans-1,2-bis(diphenylphosphinomethyl)-cyclopentane was added in place of reDPMNr. Four hours after the reaction was commenced, the conversion rate of allyl alcohol was 93.3%. It was found that 2.85 g (25.1 mmol) of 2-hydroxytetrahydrofuran and 0.729 g (6.42 mmol) of 2-methyl-3-hydroxypropanal were produced. The selectivity of 2-hydroxytetrahydrofuran was 78.2%. The selectivity of 2-methyl-3-hydroxypropanal, that of propionaldehyde and that of n-propanol were 20.0%, 0.41% and 0.19%, respectively.

COMPARATIVE EXAMPLE 5

The hydroformylation reaction of allyl alcohol was carried out in the same manner as in Example 1 except that 19.3 mg (40 µmol) of trans-1,2-bis(diphenylphosphinomethyl) cyclohexane was added in place of reDPMNr. Five hours after the reaction was commenced, the conversion rate of allyl alcohol was 51.5%. It was found that 0.51 g (5.80 mmol) of 2-hydroxytetrahydrofuran and 1.00 g (11.4 mmol) of 2-methyl-3-hydroxypropanal were produced. The selectivity of 2-hydroxytetrahydrofuran was 32.7%. The selectivity of 2-methyl-3-hydroxypropanal and that of propionaldehyde were 64.4% and 1.70%, respectively. n-Propanol was not detected.

It will be understood from the above disclosure that according to the present invention, ally alcohol can be converted into 2-hydroxytetrahydrofuran with high selectivity, which is the precursor of 1,4-butanediol, by using the diphosphine ligand (bidentate ligand) having a specific structure in the hydroformylation of allyl alcohol which comprises reacting allyl alcohol with carbon monoxide and hydrogen in the presence of a rhodium complex compound.

While the present invention has been described in detail and with reference to specific embodiments thereof, it is apparent to one skilled in the art that various changes and modifications can be made therein without departing from the spirit and the scope of the present invention.

What is claimed is:

1. A process for hydroformylation of allyl alcohol to produce 2-hydroxytetrahydrofuran which comprises reacting allyl alcohol with carbon monoxide and hydrogen in the presence of a rhodium compound and a diphosphine compound selected from the group consisting of trans-2,3-bis (diphenylphosphinomethyl)-bicyclo-[2,2,1]-heptane, trans-2,3-bis(diphenylphosphinomethyl)-bicyclo-[2,2,1]-hept-5-ene, trans-2,3-bis(diphenylphosphinomethyl)-2-methyl-bicyclo-[2,2,1]-heptane, trans-2,3-bis (diphenylphosphinomethyl)-2-methyl-bicyclo-hept-[2,2,1]-5-ene, trans-2,3-bis(diphenylphosphinomethyl)-1,4,5,6,7-pentamethyl-bicyclo-[2,2,1]-heptane, trans-2,3-bis (diphenylphosphinomethyl)-1,4,5,6,7-pentamethy-bicyclo-[2,2,1]-hept-5-ene, trans-2,3-bis(diphenylphosphinomethyl)-1,2,4,5,6,7-hexamethyl-bicyclo-[2,2,1]-heptane, and trans-2,3-bis(diphenylphosphinomethyl)-1,2,4,5,6,7-hexamethyl-bicyclo-[2]-hept-5-ene.

2. The process as in claim 1, wherein said hydroformylation is carried out further in the presence of a phosphine compound represented by formula (III)

$$PR^4R^5R^6 \quad (III)$$

wherein $R^4$ $R^5$ and $R^6$ each represents an alkyl group or a substituted or unsubstituted aryl group.

3. The process as in claim 2, wherein $R^4$ $R^5$ and $R^6$ each represents an alkyl group having 2 to 7 carbon atoms, or a substituted or unsubstituted aryl group.

4. The process as in claim 3, wherein said phosphine compound of the formula (III) is triphenylphosphine or tris(p-fluorophenyl)phosphine.

5. The process as in claim 1, wherein said diphosphine compound of is used in an amount of 0.5 to 50 mol per 1 gram-atom of rhodium.

6. The process as in claim 1, wherein said phosphine compound of is used in an amount of 2 to 500 mol per 1 gram-atom of rhodium.

7. The process as in claim 1, wherein said rhodium compound is used in an amount of $1 \times 10^{-2}$ to $1 \times 10^{-4}$ gram-atom per mol of allyl alcohol.

8. The process as in claim 1, wherein said hydroformylation reaction is carried out under pressure of 1 to 20 atm.

* * * * *